United States Patent
Lin et al.

(10) Patent No.: US 9,333,295 B2
(45) Date of Patent: May 10, 2016

(54) THERMOTHERAPY NEEDLING INSTRUMENT WITH TISSUE INJECTION

(71) Applicants: METAL INDUSTRIES RESEARCH & DEVELOPMENT CENTRE, Kaohsiung (TW); NATIONAL CHENG KUNG UNIVERSITY, Tainan (TW)

(72) Inventors: Xi-Zhang Lin, Kaohsiung (TW); Tung-Chieh Yang, Kaohsiung (TW); Tsung-Chih Yu, Kaohsiung (TW)

(73) Assignees: NATIONAL CHENG KUNG UNIVERSITY, Tainan (TW); METAL INDUSTRIES RESEARCH & DEVELOPMENT CENTRE, Kaohsiung (TW)

(*) Notice: Subject to any disclaimer, the term of this patent is extended or adjusted under 35 U.S.C. 154(b) by 0 days.

(21) Appl. No.: 14/141,325

(22) Filed: Dec. 26, 2013

(65) Prior Publication Data
US 2014/0188047 A1 Jul. 3, 2014

(30) Foreign Application Priority Data

Dec. 28, 2012 (TW) .............................. 101150965 A (51) Int. Cl.
*A61M 5/158* (2006.01)
*A61B 17/34* (2006.01)
(Continued)

(52) U.S. Cl.
CPC ............ *A61M 5/158* (2013.01); *A61B 17/3417* (2013.01); *A61B 18/1477* (2013.01);
(Continued)

(58) Field of Classification Search
CPC .......... A61B 17/3417; A61B 18/1477; A61B 2018/00821; A61B 2018/00005; A61B 2018/00023; A61B 2018/025; A61B 2018/0256; A61B 2218/002; A61M 39/10; A61M 25/007; A61M 25/00716; A61M 5/3286; A61M 5/3295–5/3298; A61M 5/1582; A61M 5/158; A61M 2025/003; A61M 2025/0681; A61M 2025/0175; A61M 25/0026–25/003; A61M 25/0071; A61M 2039/082

USPC .................. 604/533–535; 606/44, 22–26
See application file for complete search history.

(56) References Cited

U.S. PATENT DOCUMENTS 5,076,276 A * 12/1991 Sakurai ............ A61B 17/22012
601/2
5,312,400 A 5/1994 Bales et al.
(Continued)

FOREIGN PATENT DOCUMENTS

JP 2010263926 A 11/2010
TW 201008543 A 3/2010

OTHER PUBLICATIONS

Office Action and Search Report issued on May 27, 2015 by Taiwan Patent Office for the corresponding Taiwan Patent Application No. 101150965.
(Continued)

*Primary Examiner* — Bhisma Mehta
*Assistant Examiner* — Jenna Zhang
(74) *Attorney, Agent, or Firm* — WPAT, P.C., Intellectual Property Attorneys; Anthony King (57) ABSTRACT

The disclosure provides a thermotherapy needling instrument with tissue injection, including: a casing, an outer needle, an inner needle and a working needle. The casing has an inlet, an outlet and an inner channel. The outer needle is connected to the casing, and is in communication with the inner channel. The inner needle is disposed in the inner channel of the casing and the outer needle, and the inner needle has at least one opening. The at least one opening is in communication with the inner channel so that the cooling agent flows in circulation. The working needle is connected to the outer needle so as to receive the injectant for injection and tissue ablation. By using the thermotherapy needling instrument, when sampling or injection is required during thermotherapy, the injection efficacy can be achieved by withdrawing the inner needle only. Therefore, efficacy of tissue injection and ablation thermotherapy can be achieved.

10 Claims, 8 Drawing Sheets

(51) Int. Cl.
*A61M 5/32* (2006.01)
*A61M 25/06* (2006.01)
*A61M 39/08* (2006.01)
*A61B 18/14* (2006.01)
*A61B 18/00* (2006.01)

(52) U.S. Cl.
CPC ............ *A61M5/3295* (2013.01); *A61M 5/3297* (2013.01); *A61B 2018/00023* (2013.01); *A61B 2018/00821* (2013.01); *A61B 2018/1425* (2013.01); *A61B 2218/002* (2013.01); *A61M 2025/0681* (2013.01); *A61M 2039/082* (2013.01)

(56) References Cited

U.S. PATENT DOCUMENTS

| | | | |
|---|---|---|---|
| 5,951,546 A * | 9/1999 | Lorentzen | A61B 18/1477 606/41 |
| 6,506,189 B1 * | 1/2003 | Rittman et al. | 606/41 |
| 6,509,189 B1 * | 1/2003 | Tartaglia | C07K 14/715 435/252.3 |
| 7,879,031 B2 | 2/2011 | Peterson | |
| 2006/0271031 A1 * | 11/2006 | Desinger | A61B 18/1477 606/41 |
| 2007/0073285 A1 * | 3/2007 | Peterson | A61B 18/1477 606/41 |
| 2007/0171506 A1 * | 7/2007 | Jordan | G01K 11/12 359/288 |
| 2008/0161890 A1 * | 7/2008 | Lafontaine | A61B 18/1492 607/105 |
| 2011/0060326 A1 * | 3/2011 | Smith | A61B 18/18 606/33 |
| 2013/0178842 A1 * | 7/2013 | Reid, Jr. | A61B 18/1815 606/33 |

OTHER PUBLICATIONS

English translation of the Search Report issued on May 27, 2015 by Taiwan Patent Office for the corresponding Taiwan Patent Application No. 101150965.

English abstract translation of JP2010263926A, publication date: Nov. 25, 2010.

English abstract translation of TW201008543A, publication date: Mar. 1, 2010.

* cited by examiner

THERMOTHERAPY NEEDLING INSTRUMENT WITH TISSUE INJECTION

BACKGROUND OF THE INVENTION

1. Field of the Invention

The present disclosure relates to a thermotherapy needling instrument, more particularly to a thermotherapy needling instrument with tissue injection.

2. Description of the Related Art

When primary tumors or scattered small lesions are detected, minimally invasive tumor ablation, including electromagnetic thermoablation, radiofrequency ablation (RFA), and microwave ablation (MWA), can be used for treatment. These techniques have been applied to local tumor treatment, but thermotherapy needling instruments employed therein are complex in design and expensive, and lack an injection function in use. Many patients cannot receive treatment due to the expense of thermotherapy needling instruments; and even during treatment, a patient feels uncomfortable as the treatment or injection needling instrument is inserted into and taken out of the human body for many times, which causes many restrictions in treatment.

Using a radiofrequency ablation needle, which is an existing product, as an example, an effective working range of circulation of an internal cooling system thereof is limited to a tip portion only. When ethyl alcohol or medicine needs to be injected before and after ablation or during the treatment, an additional needle or instrument needs to be inserted to meet the requirement, which delays the treatment, makes the patient uncomfortable, and increases the risk of the treatment.

SUMMARY OF THE INVENTION

The present disclosure provides a thermotherapy needling instrument with tissue injection. The thermotherapy needling instrument includes: a casing, an outer needle, an inner needle, and a working needle. The casing has an inlet, an outlet, and an inner channel. The inner channel connects the inlet and the outlet, and is used for an injectant or a cooling agent to flow in. The outer needle is connected to the casing, and is in communication with the inner channel. The inner needle is disposed in the inner channel of the casing and the outer needle, and the inner needle has at least one opening The at least one opening is in communication with the inner channel so that the cooling agent flows in circulation. The working needle is connected to the outer needle so as to receive the injectant for injection and tissue ablation.

By using the thermotherapy needling instrument with tissue injection of the present disclosure, when sampling or injection is required during thermotherapy, the injection efficacy can be achieved by withdrawing the inner needle only, thereby solving the disadvantage of many times of thermotherapy or injection needling instrument removal and insertion in the prior art. Therefore, the diagnosis and treatment time can be reduced, and the treatment risk can be lowered so as to achieve efficacy of tissue injection and ablation thermotherapy.

DETAILED DESCRIPTION OF THE INVENTION

Figure 1:
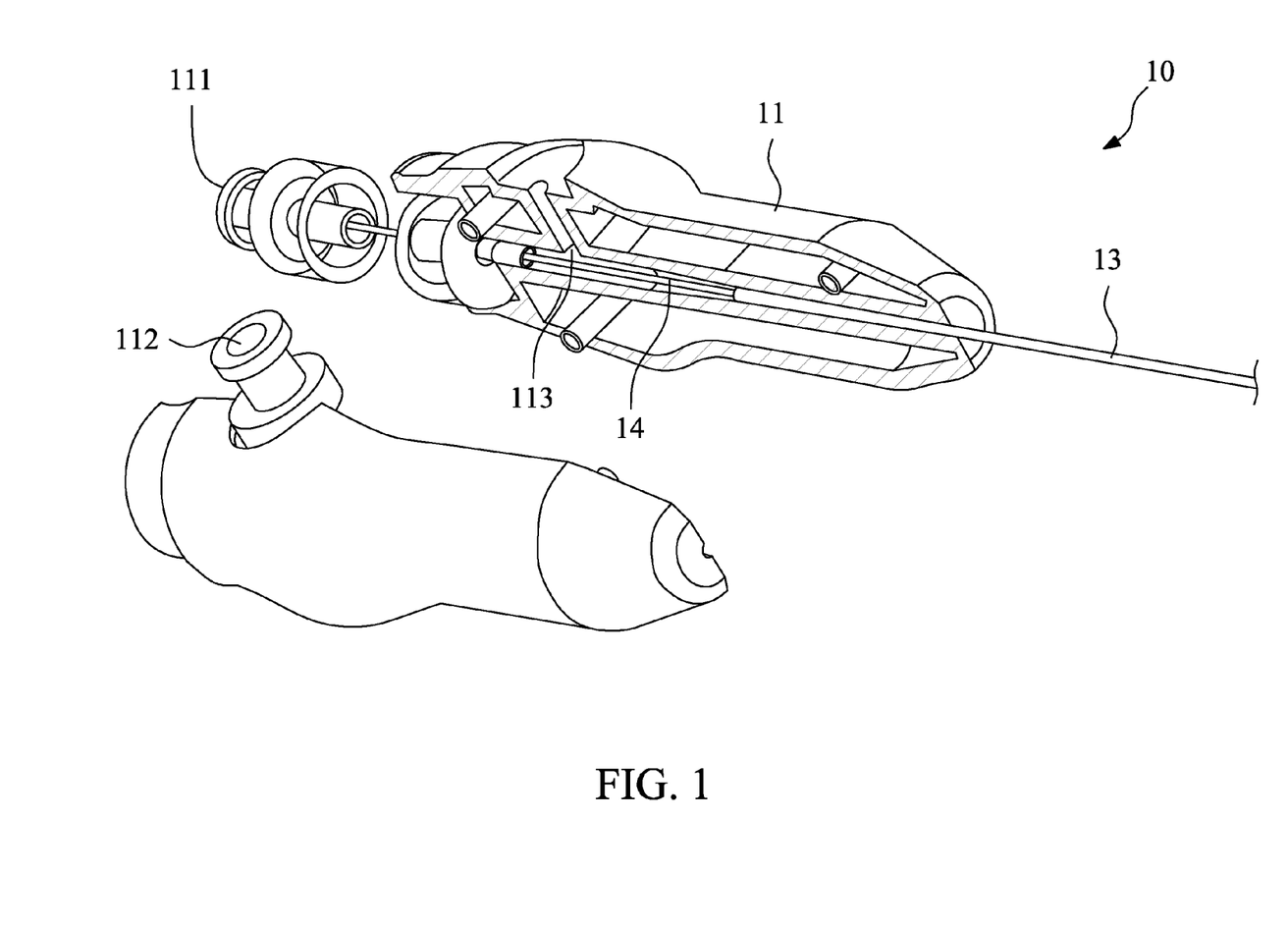
FIG. 1 shows an exploded schematic view of a casing of a thermotherapy needling instrument with tissue injection according to the present disclosure.
Figure 2:
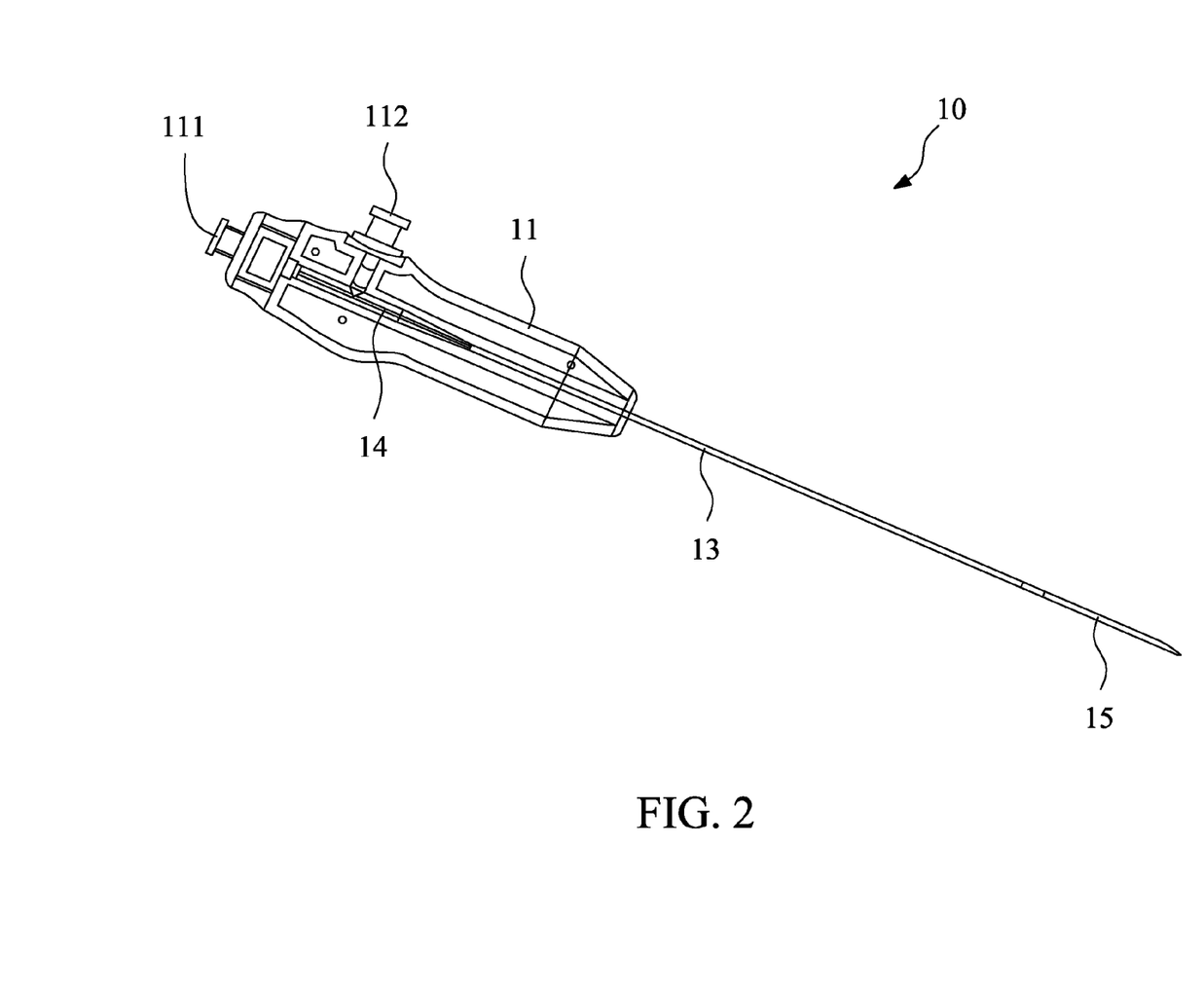
FIG. 2 shows an assembly schematic view of the thermotherapy needling instrument with tissue injection according to the present disclosure.
Figure 3:
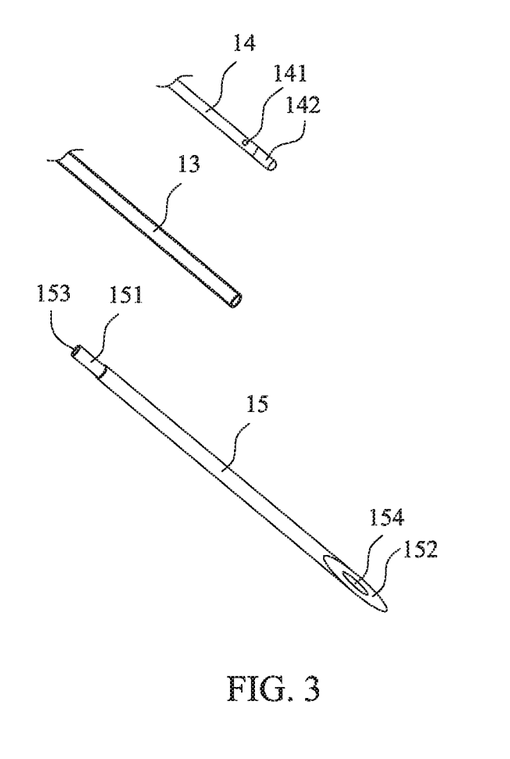
FIG. 3 shows an exploded schematic view of an outer needle, an inner needle, and a working needle of a thermotherapy needling instrument with tissue injection according to a first embodiment of the present disclosure.
Figure 4:
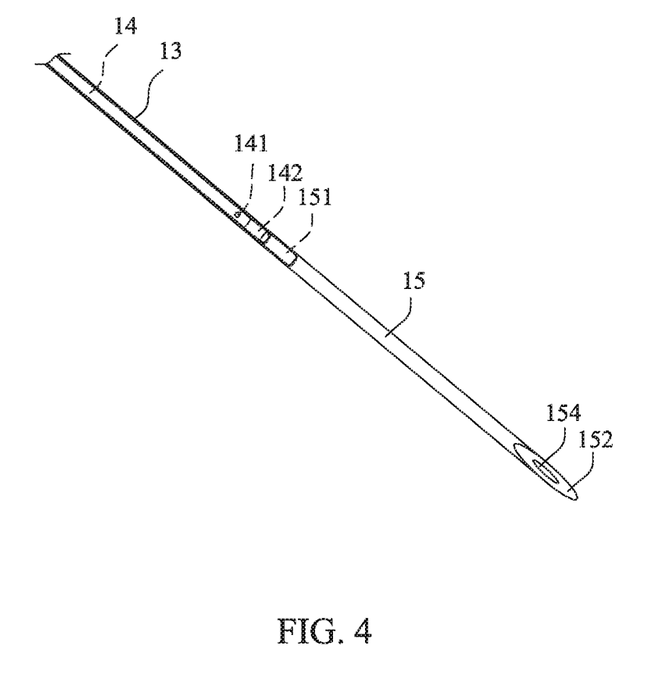
FIG. 4 shows an assembly schematic view of the outer needle, the inner needle, and the working needle of the thermotherapy needling instrument with tissue injection according to the first embodiment of the present disclosure.
Figure 5:
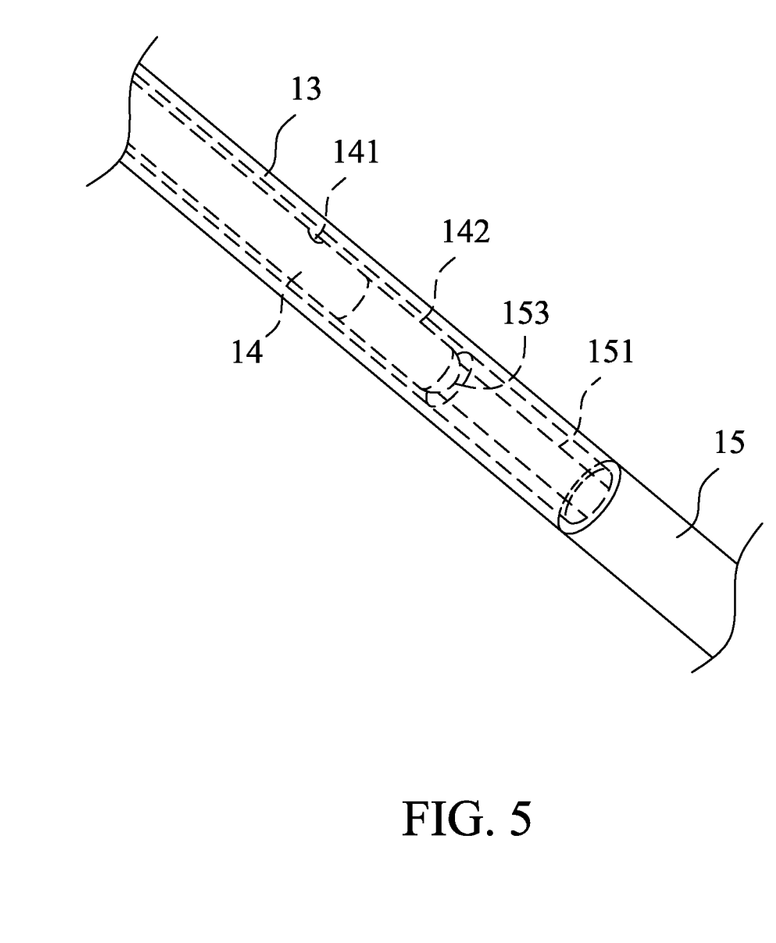
FIG. 5 shows a partial enlarged assembly schematic view of the outer needle, the inner needle, and the working needle of the thermotherapy needling instrument with tissue injection according to the first embodiment of the present disclosure.

FIG. 1 shows an exploded schematic view of a casing of a thermotherapy needling instrument with tissue injection according to the present disclosure. FIG. 2 shows an assembly schematic view of the thermotherapy needling instrument with tissue injection according to the present disclosure. FIG. 3 shows an exploded schematic view of an outer needle, an inner needle, and a working needle of a thermotherapy needling instrument with tissue injection according to a first embodiment of the present disclosure. FIG. 4 shows an assembly schematic view of the outer needle, the inner needle, and the working needle of the thermotherapy needling instrument with tissue injection according to the first embodiment of the present disclosure. FIG. 5 shows a partial enlarged assembly schematic view of the outer needle, the inner needle, and the working needle of the thermotherapy needling instrument with tissue injection according to the first embodiment of the present disclosure.

Referring to FIG. 1 to FIG. 5, according to the present disclosure a thermotherapy needling instrument 10 with tissue injection includes: a casing 11, an outer needle 13, an inner needle 14, and a working needle 15. The casing 11 has an inlet 111, an outlet 112, and an inner channel 113. The inner channel 113 connects the inlet 111 and the outlet 112, and is used for an injectant or a cooling agent to flow in.

A tail end of the inner needle 14 is disposed in the casing 11, and is connected to the inlet 111. In this embodiment, the inner channel 113 surrounds the inner needle 14.

A tail end of the outer needle 13 is connected in the casing 11, and is in communication with the inner channel 113. A front end of the inner needle 14 is disposed in the outer needle 13, and the inner needle 14 has at least one opening 141. The at least one opening 141 is in communication with the inner channel 113, so that the cooling agent flows in circulation. Preferably, the at least one opening 141 is adjacent to the front end of the inner needle 14.

The working needle 15 is connected to the outer needle 13 so as to receive the injectant for injection and tissue ablation. Moreover, the working needle 15 can be used for thermotherapy, and different materials can be selected to design the working needle 15 for hermotherapy treatment using different systems (for example, a radio frequency system, an electromagnetic system, or a microwave system).

In this embodiment, the working needle 15 has a connection end 151 and a front end 152. The connection end 151 is disposed in the outer needle 13, and can be fixed by using an adhesive.

The front end of the inner needle 14 has an abutting end 142 used for abutting against a communication hole 153 of the connection end 151. An outer diameter of the inner needle 14 is less than an inner diameter of the outer needle 13, and the outer diameter of the inner needle 14 is spaced by a gap from the inner diameter of the outer needle 13. The at least one opening 141 is in communication with the inner channel 113 through the gap.

Therefore, when the thermotherapy needling instrument of the present disclosure is applied to thermotherapy, after entering the inner needle 14 from the inlet 111, the cooling agent (such as cooling water) flows through the inner needle 14. Then, the cooling agent flows out from the at least one opening 141 to the gap and the inner channel 113, and flows out from the outlet 112, thereby forming a cooling circulation. In addition, since the abutting end 142 of the inner needle 14 abuts against the communication hole 153 of the connection end 151, the cooling agent will not flow to the working needle 15.

When the thermotherapy needling instrument of the present disclosure needs to inject medicine during thermotherapy, it is only necessary to withdraw and remove the inner needle 14 and feed the injectant (such as medicine) into the inner channel 113 while the working needle 15 that has been embedded in the human body does not need to be removed. The inner needle 14 is removeable. The working needle 15 has an injection hole 154 for injection. The injectant can flow to the communication hole 153 of the working needle 15 through the outer needle 13, and is injected into the human body through the front end 152 and the injection hole 154 of the working needle 15.

Therefore, by using the thermotherapy needling instrument with tissue injection of the present disclosure, when sampling or injection is required during thermotherapy, the injection efficacy can be achieved by withdrawing the inner needle 14 only, thereby solving the disadvantage of many times of thermotherapy or injection needling instrument removal and insertion in the prior art. Therefore, the diagnosis and treatment time can be reduced, and the treatment risk can be lowered so as to achieve efficacy of tissue injection and ablation thermotherapy.

Figure 6:
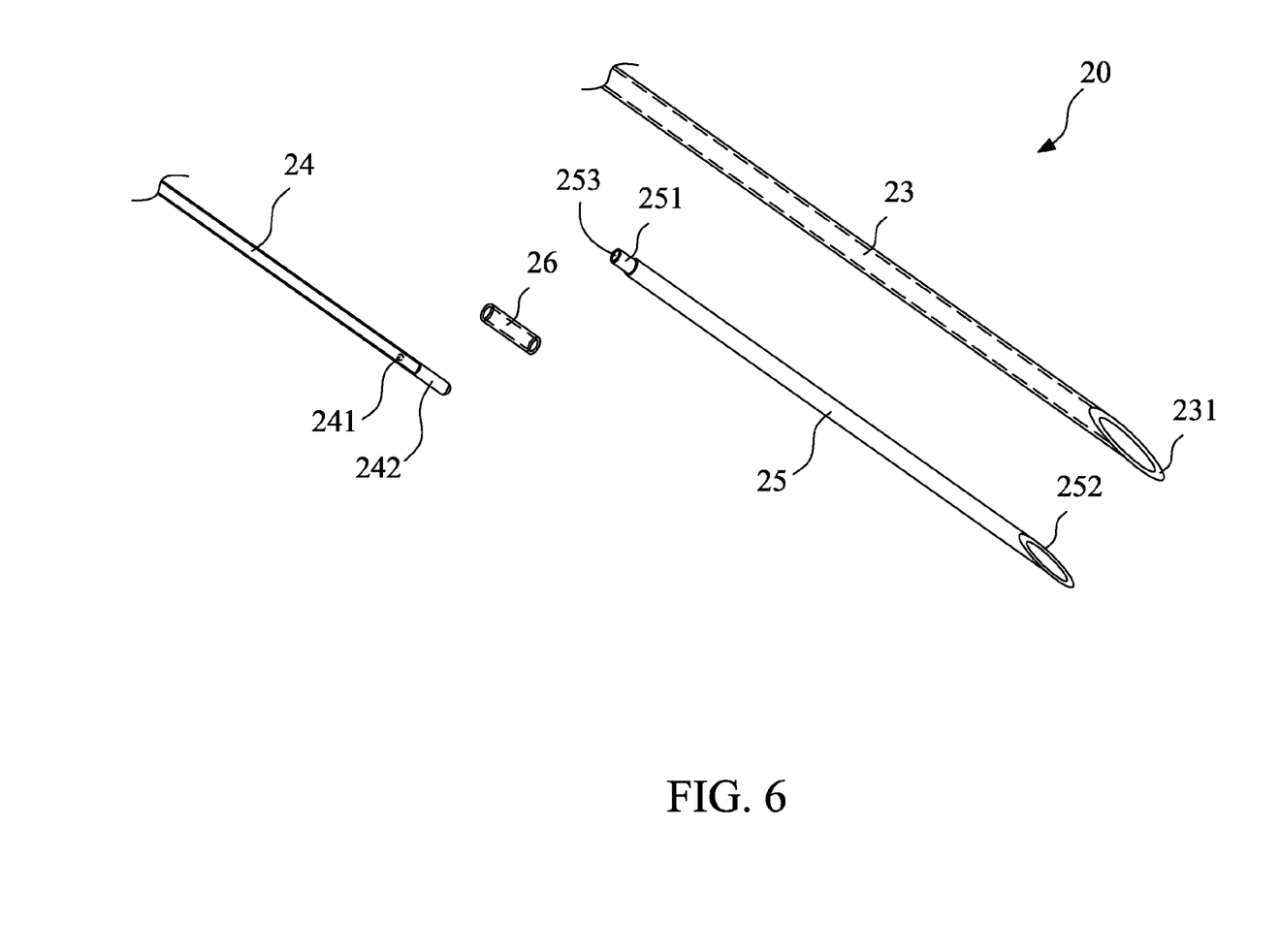
FIG. 6 shows an exploded schematic view of an outer needle, an inner needle, and a working needle of a thermotherapy needling instrument with tissue injection according to a second embodiment of the present disclosure.
Figure 7:
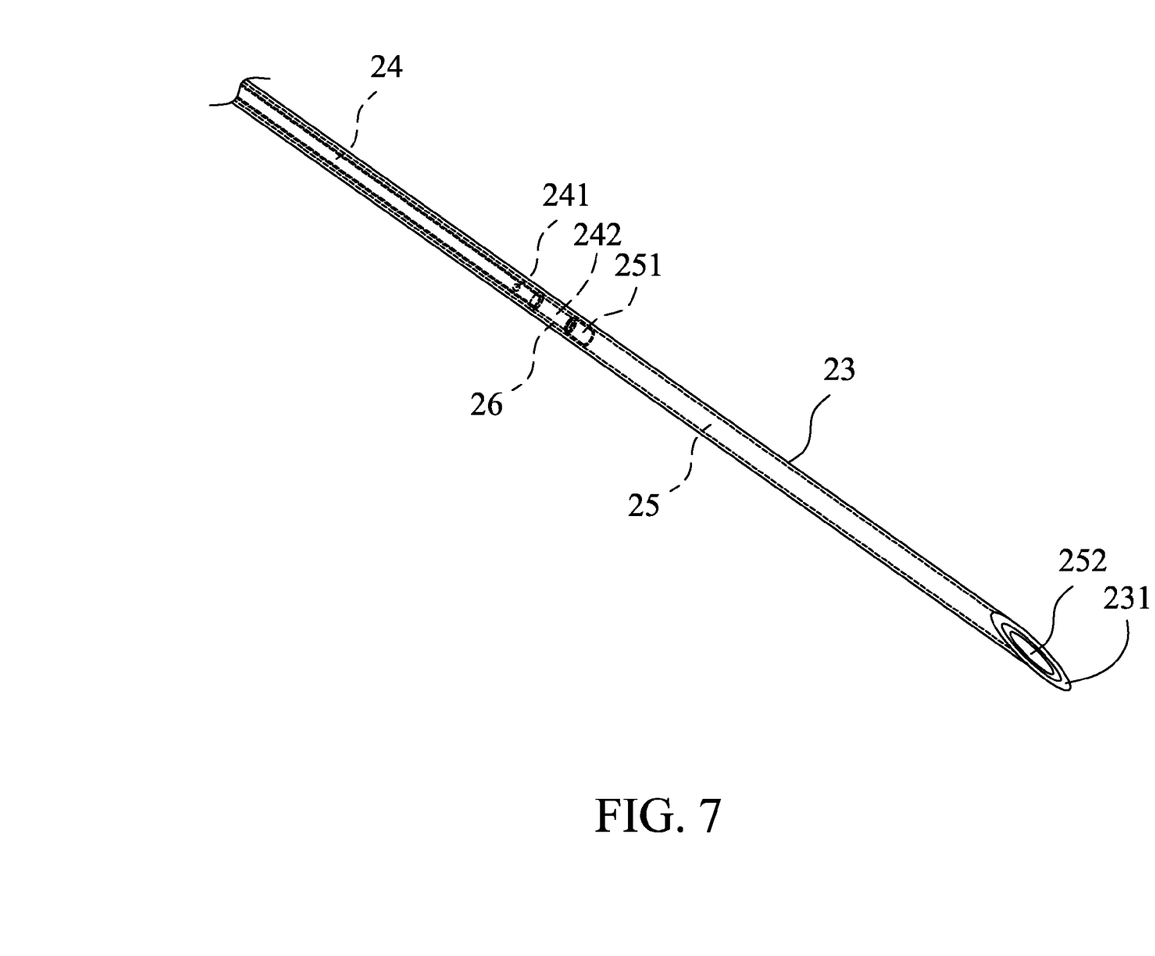
FIG. 7 shows an assembly schematic view of the thermotherapy needling instrument with tissue injection according to the second embodiment of the present disclosure.
Figure 8:
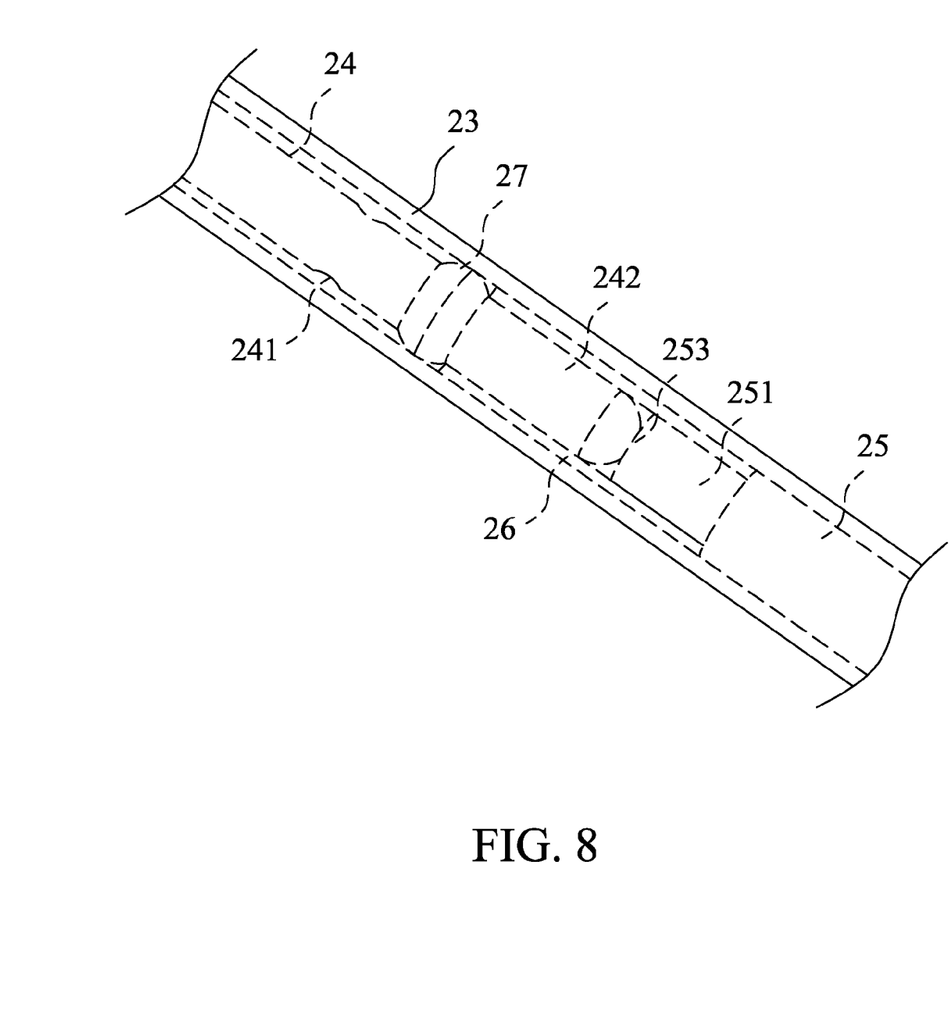
FIG. 8 shows a partial enlarged assembly schematic view of the outer needle, the inner needle, and the working needle of the thermotherapy needling instrument with tissue injection according to the second embodiment of the present disclosure.

FIG. 6 shows an exploded schematic view of an outer needle, an inner needle, and a working needle of a thermotherapy needling instrument with tissue injection according to a second embodiment of the present disclosure. FIG. 7 shows an assembly schematic view of the thermotherapy needling instrument with tissue injection according to the second embodiment of the present disclosure. FIG. 8 shows a partial enlarged assembly schematic view of the outer needle, the inner needle, and the working needle of the thermotherapy needling instrument with tissue injection according to the second embodiment of the present disclosure.

Referring to FIG. 6 to FIG. 8, the difference between the thermotherapy needling instrument 20 according to the second embodiment and the thermotherapy needling instrument 10 according to the first embodiment lies in that structures of an outer needle 23, an inner needle 24, and a working needle 25. In this embodiment, the working needle 25 is disposed in the outer needle 23, and may be fixed by using an adhesive. The outer needle 23 has a front end portion 231, and the working needle 25 has a connection end 251 and a front end 252. The shape of the front end portion 231 matches with the shape of the front end 252. Therefore, in the thermotherapy needling instrument according to the second embodiment of the present disclosure, a part of the outer needle 23 is inserted into the human body to perform thermotherapy or injection.

The inner needle 24 has an abutting end 242 used for abutting against a communication hole 253 of the connection end 25. The thermotherapy needling instrument 20 according to the second embodiment of the present disclosure further includes a covering ring 26. The connection end 251 and the abutting end 242 are respectively disposed in two ends of the covering ring 26. In addition, the thermotherapy needling instrument 20 according to the second embodiment of the present disclosure further includes an O-shaped ring 27 disposed between the abutting end 242 of the inner needle 24 and the at least one opening 241 to prevent the cooling agent from flowing to the working needle 25.

Similarly, the thermotherapy needling instrument according to the second embodiment of the present disclosure can have the efficacy of the thermotherapy needling instrument according to the first embodiment of the present disclosure.

In addition, the thermotherapy needling instrument according to the present disclosure may further include a thermocouple (which is not shown in the drawings) disposed in the inner needle, or disposed on a wall of the outer needle to detect the temperature of the thermotherapy needling instrument.

While several embodiments of the present disclosure have been illustrated and described, various modifications and improvements can be made by those skilled in the art. The embodiments of the present disclosure are therefore described in an illustrative but not in a restrictive sense. It is intended that the present disclosure should not be limited to the particular forms as illustrated and that all modifications which maintain the spirit and scope of the present disclosure are within the scope defined in the appended claims.

What is claimed is:

1. A thermotherapy needling instrument with tissue injection, comprising:
   a casing having an inlet, an outlet, and an inner channel, the inner channel connected to the inlet and the outlet, and used for an injectant or a cooling agent to flow in;
   an outer needle connected to the casing, and being in communication with the inner channel;
   an inner needle disposed in the inner channel of the casing and the outer needle, and having at least one opening, the at least one opening being in communication with the inner channel so that the cooling agent flows in circulation, the inner needle being removeable; and
   a working needle connected to the outer needle to receive the injectant for injection and tissue ablation after the inner needle is removed, with the working needle having an injection hole for injection.

2. The thermotherapy needling instrument according to claim 1, wherein the working needle has a connection end and a front end, and the connection end is disposed in the outer needle.

3. The thermotherapy needling instrument according to claim 2, wherein the inner needle has an abutting end used for abutting against a communication hole of the connection end.

4. The thermotherapy needling instrument according to claim 1, wherein an outer diameter of the inner needle is less than an inner diameter of the outer needle, and the outer diameter of the inner needle is spaced by a gap from the inner diameter of the outer needle, the at least one opening is in communication with the inner channel through the gap.

5. The thermotherapy needling instrument according to claim 1, wherein the working needle is disposed in the outer needle; the outer needle has a front end portion, and the working needle has a connection end and a front end, the shape of the front end portion of the outer needle matches with the shape of the front end of the working needle.

6. The thermotherapy needling instrument according to claim 5, wherein the inner needle has an abutting end used for abutting against a communication hole of the connection end.

7. The thermotherapy needling instrument according to claim 6, further comprising a covering ring, wherein the connection end and the abutting end are respectively disposed in two ends of the covering ring.

8. The thermotherapy needling instrument according to claim 6, further comprising an O-shaped ring disposed between the abutting end of the inner needle and the at least one opening.

9. The thermotherapy needling instrument according to claim 1, further comprising a thermocouple disposed in the inner needle.

10. The thermotherapy needling instrument according to claim 1, further comprising a thermocouple disposed on a wall of the outer needle.

\* \* \* \* \*